United States Patent [19]

Eichler

[11] Patent Number: 4,558,710
[45] Date of Patent: Dec. 17, 1985

[54] TESTING OF THE AIRWAYS AND PULMONARY TRACT OF A PATIENT, PARTICULARLY FOR SENSITIVITY TO AEROSOLS

[75] Inventor: Rüdiger Eichler, Zellingen, Fed. Rep. of Germany

[73] Assignee: Erich Jaeger GmbH & Co., Hoechberg, Fed. Rep. of Germany

[21] Appl. No.: 611,372

[22] Filed: May 16, 1984

Related U.S. Application Data

[63] Continuation of Ser. No. 274,527, Jun. 17, 1981, abandoned.

[30] Foreign Application Priority Data

Jun. 24, 1980 [DE] Fed. Rep. of Germany ....... 3023648

[51] Int. Cl.$^4$ ............................................... A61B 5/08
[52] U.S. Cl. ..................................... 128/720; 128/725
[58] Field of Search ....................... 128/200.19, 200.21, 128/719, 720, 725, 743, 747; 222/57, 61, 638, 644, 645, 649

[56] References Cited

U.S. PATENT DOCUMENTS

| 3,498,294 | 3/1970 | Zeff et al. | 128/719 |
| 4,106,503 | 8/1978 | Rosenthal et al. | 128/194 |
| 4,259,967 | 4/1981 | Vooren et al. | 128/720 |
| 4,265,248 | 5/1981 | Chuiton et al. | 128/747 |

FOREIGN PATENT DOCUMENTS

| 883449 | 9/1980 | Belgium | 128/720 |
| 2649876 | 5/1978 | Fed. Rep. of Germany | 128/720 |
| 2055046 | 2/1981 | United Kingdom | 128/200.19 |

Primary Examiner—Edward M. Coven
Assistant Examiner—Max F. Hindenburg
Attorney, Agent, or Firm—Frishauf, Holtz, Goodman & Woodward

[57] ABSTRACT

To permit accurate introduction of aerosols containing, for example, irritants or similar substances, into the pulmonary tract or airways of a patient, the breathing cycles of the patient are counted and, after a number of normal breathing cycles, and during a limited period of time in the inhalation phase of a breathing cycle, and after commencement of the inhalation phase, a predetermined quantity of aerosols is introduced to the patient by applying compressed air of controlled pressure to an atomizer or aerosol fog generator (32, 34); initiation of inhalation is sensed, for example by a pressure transducer (24), the output of which is connected to a threshold stage (50) sensing inhalation and exhalation, respectively, and setting a time delay period for example of less than half than normal duration of the inhalation phase of the patient, which then triggers a timing interval by a monostable flip-flop (56) which, during the time period thereof, applies the controlled compressed air to the atomizer (32, 34), the compressed air being shut off, and thus terminating atomization well in advance of the end of the inhalation cycle, and preferably less than ½ second, for example less than 0.3 second, so that the quantity of aerosols is accurately controlled and will reach the alveoli to be absorbed in the lungs so that the breathing tube will be essentially free from contaminating aerosols.

20 Claims, 3 Drawing Figures

TESTING OF THE AIRWAYS AND PULMONARY TRACT OF A PATIENT, PARTICULARLY FOR SENSITIVITY TO AEROSOLS

This application is a continuation of application Ser. No. 274,527, filed June 17, 1981, abandoned.

The present invention relates to medical diagnosis, and more particularly to the testing of the airways and the pulmonary tract of a patient, particularly to determine sensitivity to aerosols.

BACKGROUND

Various types of apparatus have been proposed to test breathing response of patients. One such apparatus is known under the name "Astograph". The patent literature also describes apparatus of this type, see, for example, German Utility Model DE-GM No. 79 14 971 U1.

Patients who have asthma have intervals free from attacks; even in those intervals, however, the bronchial system is excessively sensitive to external irritants, for example various types of aerosols. It is possible to trigger a bronchial spasm in such patients by controlled inhalation of substances to which the patients are allergic, or to other particularly active substances. Such spasms can be determined by sensing an increase in resistance in the airways of the patient. This resistance increase is reversible. It is desirable to be able to determine particular substances which cause excessive irritation, so that treatment can be devised for healing or at least reducing the debilitating effects of such irritants. It is thus necessary to be able to determine to which substances the patient is allergic, that is, which substances trigger asthmatic attacks. This has been done, usually, by means of an asthma-provocation test, in which the patient is asked to breath an aerosol which contains a substance to which he may be allergic in atomized form, for example as prepared or provided by a small fog generator.

The usual method of testing the patient was this: During a predetermined period of time, which covered a substantial number of breathing cycles, that is, inhaling and exhaling cycles, an allergen-aerosol was also permitted to be inhaled. Thereafter, the air flow resistance was measured. If the patient did not have an adverse reaction, the concentration of the allergen was increased, and the test repeated, until a certain air flow resistance was exceeded. The referenced German Utility Patent DE-GM No. 79 14 971 U1 describes an apparatus in which the flow resistance of the airways of the patient can be measured almost continuously during the inhalation phase of the breathing cycle. A valve was placed between the atomizing substance and a mouthpiece which the patient used, and which opened upon breathing-in or inhalation by the patient; a branch line was taken off between the valve and the mouthpiece which was connected to a measuring device to measure the flow resistance of the airway or air path upon exhalation. Such a device is capable of rapidly determining even a tendency to obstruction of the airway or pulmonary path of the patient, that is, an initial obstruction or beginning of obstruction condition, so that, by quick application of a counter-acting medication, formation of a severe obstruction could be promptly inhibited. Reference is made to U.S. Pat. No. 3,857,385, Hampl, assigned to the assignee of this application, and to U.S. Pat. No. 4,259,967, Vooren et al., for general discussions of measuring respiratory resistance and parameters.

THE INVENTION

It is an object to improve testing of the airways or pulmonary tract of patients, particularly testing of patients for their sensivity to aerosol, in which the quantity of aerosol to be inhaled by the patient can be more accurately determined; which permits easy and rapid switch-over between different allergens or medication, and which does not require complicated cleaning of the apparatus upon switch-over from one allergen to another one.

Briefly, the mouthpiece is closely coupled to an atomizer, which is directly and continuously connected thereto, and positioned closely adjacent thereto. The atomizing effect is permitted to occur only under control of a control system which controls application of atomizing energy, for example of compressed air from a controlled compressed air source, to the atomizer or aerosol fog generator. The aerosol fog generator or atomizer contains an irritant. An irritant controller is provided coupled to and responsive to changes in the air flow in the air duct coupled to the mouthpiece and responsive to the inhaling phase of the patient. The controller is connected to control the application of atomizing energy, for example compressed air, during only a portion of the inhaling phase, preferably occurring during the first $\frac{2}{3}$ and especially during the first $\frac{1}{2}$ of the inhalation phase of a breathing cycle. The duration of operation of the atomizer or aerosol fog generator is short, preferably less than about 300 milliseconds, and preferably not exceeding about 500 milliseconds.

More than one atomizer or fog generator may be controlled by the system, some of which may contain irritants, and some of which may not, but rather contain neutral substances. The control means can additionally be so set, preferably by use of a counter, that the irritant aerosol is applied only from time to time, that is, after a selected number of breathing cycles, for example for every 50th or 100th breathing cycle, and then, as aforesaid, only for a fraction of the inhaling phase thereof, to be stopped until the next recurrence after the next breathing cycle determined by the setting of the counter during which aerosol is again to be supplied.

DRAWINGS

DETAILED DESCRIPTION

Figure 1:
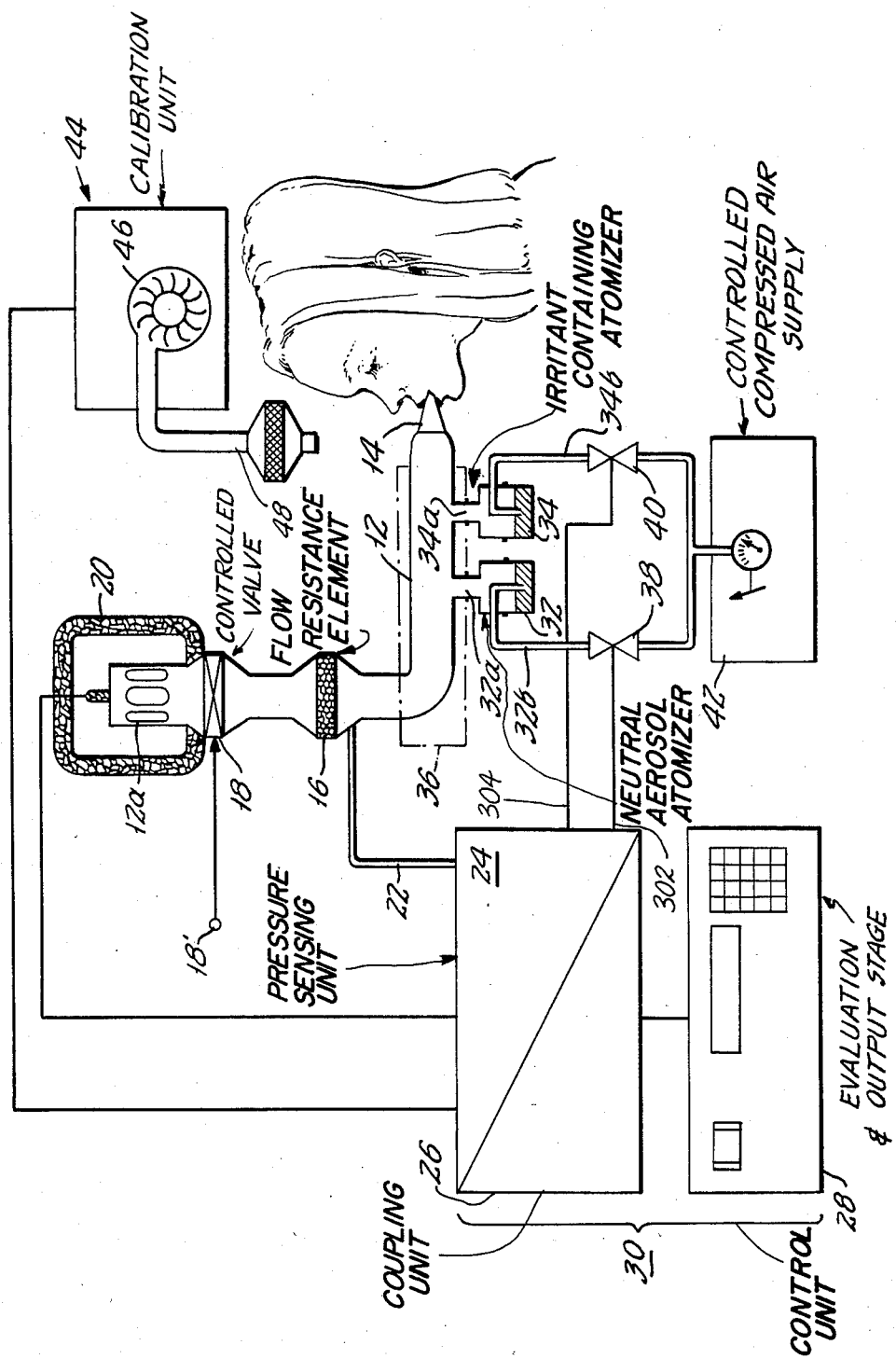
FIG. 1 is a schematic view of an apparatus in accordance with a preferred embodiment of the invention.

The apparatus—see FIG. 1—includes a single breathing tube or duct 12 which has a mouthpiece 14 adapted to be gripped by a patient 10, so that the airways or the pulmonary tract of the patient can be tested for its reaction to irritants and allergens. The breathing tube 12 includes a flow resistance element 16, for example in form of a metal mesh cartridge and, connected thereto, a rapid operating electromagnetic valve 18. The outlet end 12a of the breathing tube 12 is surrounded by a filter 20 in order to prevent escape of aerosols into ambient air.

The side of the flow resistance element 16 facing the mouthpiece 14 is connected to a pressure sensing unit 24 by a pressure measuring line 22. The pressure sensing unit, or element 24 is located in a coupling unit 26 which is connected to an evaluation and output stage 28 to form, together therewith, a control unit 30 which controls operation of the entire system and which processes the data derived during the examination of the patient.

The portion of the breathing tube 12 between the mouthpiece 14 and the throttling of flow resistance element 16 is coupled to outlets 32a, 34a from atomizers r aerosol-fog producing elements 32, 34, respectively. In a preferred form, more than one such atomizer is connected to the breathing tube. The drawing shows two such atomizer or aerosol fog generator units 32, 34. The atomizers or aerosol fog generators 32, 34, and such other elements or units as may be connected, can be units of commercial customary devices, operated with compressed air and connected to a controlled compressed air supply source 42. The units 32, 34 are directly connectable to a block 36, illustrated only schematically, and forming a part of the breathing tube 12. The connection of the units 32, 34 preferably is severable, and includes quick-connecting devices.

In a preferred form, no intermediate element such as a valve or the like is connected between the aerosol outputs of the atomizers or fog generators 32, 34, respectively, and the breathing tube 12. The connection should terminate close to the mouthpiece 14 in the breathing tube 12, so that elaborate cleaning to remove aerosols introduced into the breathing tube and not desired in a subsequent test will not be necessary.

The aerosol fog generators or atomizers 32, 34 are connected to the compressed air source by a compressed air connection 32b, 34b, respectively, which forms a controlled input to supply the necessary operating energy to generate the aerosol fog or to cause the atomization of the substances included within the respective elements 32, 34. The compressed air connections 32b, 34b are respectively connected over magnetic valves 38, 40 to the controlled compressed air supply 42. The air supply 42 includes a pressure regulator and supplies compressed air at a constant, adjustable and selectable air pressure.

The apparatus further includes a calibration unit 44 which has a blower 46 providing a predetermined air flow and which has an output line 48 which can be connected to the breathing tube 12 instead of the mouthpiece 14 to provide a controlled air flow through the breathing tube 12 for initial calibration purposes. A signal representative of standard, calibrating air flow is transmitted to pressure sensing unit 24, which also receives a signal representative of ambient air pressure in filter 20 to permit flow calibration of unit 24.

Figure 2:
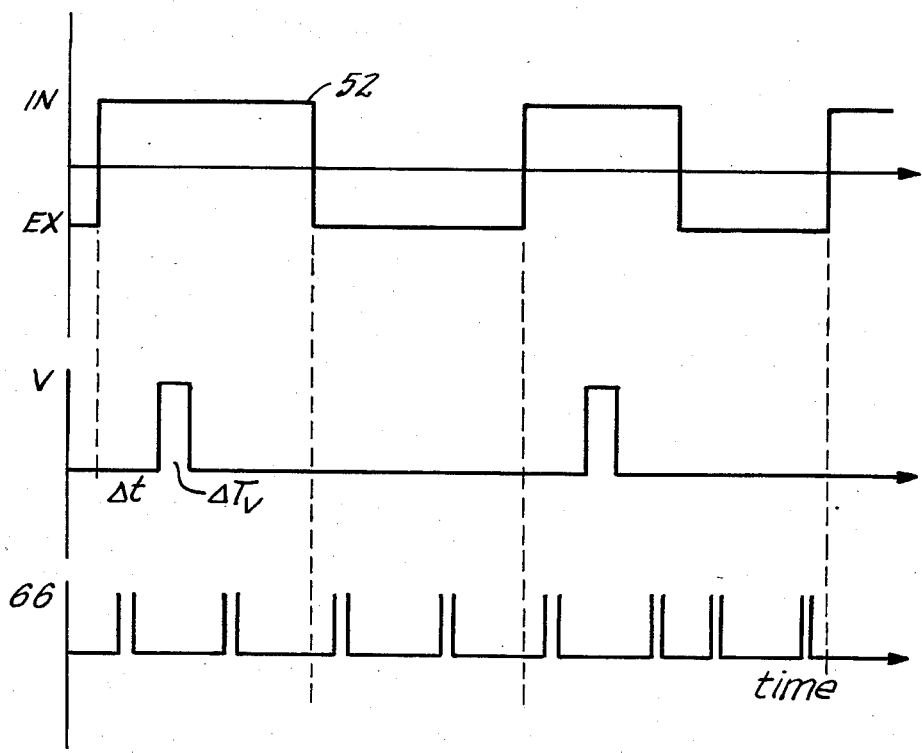
FIG. 2 is a series of timing diagrams and graphs illustrating the method of application of aerosols and the operation of the apparatus.
Figure 3:
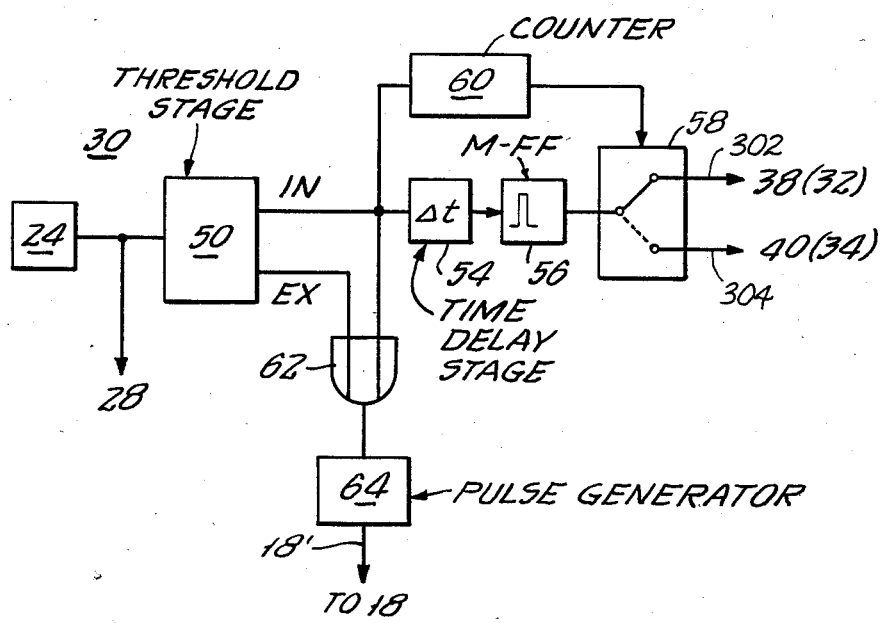
FIG. 3 is a schematic circuit diagram illustrating a portion of the control system of the apparatus of FIG. 1.

Control system, with reference to FIG. 3: The lines 302, 304 (FIG. 1) schematically show signal transfer from pressure control unit 30 to the valves 38, 40. The details of the transfer paths are shown in FIG. 3. The pressure sensing unit, or device 24 of control unit 30 has an electrical output which is connected to a threshold stage 50. The threshold stage 50 has two outputs IN and EX. The outputs IN and EX, respectively, will have signals appear thereat during the inhaling and exhaling phase, respectively, of a breathing cycle. The outputs from unit 50 are shown in curve 52, FIG. 2, depending on the direction of air flow within the breathing tube 12. If the pressure indicator 24 shows that the patient is inhaling, that is, if the IN terminal of threshold stage 50 is active, then the signal from the threshold stage 50 is applied to a time delay stage 54 which initiates a timing interval $\Delta t$. The time delay $\Delta t$, preferably, is adjustable. After the time delay, which is set to occur after commencement of breathing-in by the patient, a pulse is provided to a monostable flip-flop (M-FF) 56. The M-FF 56 provides an output pulse, the duration of which is preferably also adjustable, which controls the input of a switch 58, shown as a transfer switch. The switch 58 has a first output which is connected to the valve 38 of the atomizer 32, and a second output connected to the valve 40 for the atomizer 34. In a preferred form, at least two atomizers are provided, although only one of them is strictly necessary. If the atomizer 32 contains a pure, or biologically neutral and non-irritating substance, whereas the atomizer 34 contains a solvent which includes irritants, then the output of the M-FF 56 is connected in the quiescent or stable state through switch 58 to the valve 38, and hence to the neutral or non-irritant atomizer. If no such atomizer is provided, the M-FF output will be connected to control the switch 58 to be OFF.

Transfer of the switch 58 from the solid-line position to the broken-line position is controlled by a counter 60. The counter 60 also has the IN signal applied thereto derived from the threshold stage 50. The count state of the counter 60 is adjustable. Counter 60 counts the number of breathing cycles or, more accurately, the number of inhaling steps made by the patient. By suitable setting of the counter 60, the ratio of the number of breathing cycles during which the switch 58 transfers from solid-line to broken-line-position to provide aerosols with irritant, with respect to the number of breathing cycles during which no irritant is supplied will then be controlled in accordance with settings determined by the physician or test operator. Suitable ranges, which determine the possible count states of the counter, are 1 breathing cycle with irritant to 10 breathing cycles without irritant and 1:100.

The outputs IN and EX are further connected over an OR-gate 62 to a pulse generator 64 which provides one or more pulses 66 (see FIG. 2) during each inhaling and exhaling phase of the breathing cycle to close the valve 18, by providing output signals at terminal 18'. The air flow resistance of the air path or the pulmonary tract of the patient can thereby be determined in accordance with the blocking pressure principle, as well known.

The output of the pressure sensing device 24 is additionally connected to an evaluation and output stage 28 which includes a computer element which can provide output graphs of flow curves of the air being breathed by the patient, as well known.

Operation, with specific reference to FIG. 2 and also FIGS. 1 and 3.

One or more pulses 66 are generated at the beginning and during a later portion of any inhaling and exhaling phase of the breathing cycle which cause closure of the valve 18, so that a pressure corresponding to alveolar pressure will build up in the breathing tube 12. This pressure transmitted by tube 20 to pressure sensor 24, together with the flow speed of air within the breathing tube 12 before the valve 18 has closed, permits calculation of the airway resistance or pulmonary resistance of the patient, in accordance with well known techniques. The referenced U.S. Pat. Nos. 3,857,385 and 4,259,967 describe suitable techniques. All atomizers 32, 34 are out of connection, that is, valves 38, 40 are both closed at the beginning of any examination of the patient. It is possible, however, to connect a fog generator or atomizer 32 which contains merely aerosol solvents without any irritating or stimulating or polluting or other agents.

Upon initiation of the actual test of the patient for asthma or the like, counter 60 is so adjusted that it provides a transfer pulse to switch 58 only for each 100 breathing cycles. The delay stage 54 receives an input pulse upon initiation of each inhaling cycle. After termination of the delay time Δt, the M-FF 56 is triggered and provides a fog generating pulse V—see second graph of FIG. 2. This V-pulse is applied to the valve 40 via switch 58—in broken-line position, under control of counter 60 to permit application of compressed air from the controlled supply 42 to the atomizer 34 if the transfer switch 58 has been placed from solid-line into broken-line position. The pulse length determined by pulse 56 is short, and less than the entire inhaling phase of a breathing cycle. Preferably, the duration of the time during which the atomizer is operating, that is, has air connected from the compressed air supply, is substantially less than a normal inhaling phase of a breathing cycle, and may, for example, be in the order of about 0.1 to 0.3 seconds, as seen at $\Delta T_V$ in the second line of the graphs of FIG. 2. The range is not critical and can be adjusted by suitable adjustment of the pulse time of the M-FF 56, for example by changing a resistance value of an R/C circuit as well known in M-FF units. A suitable adjustment range, for example, is in order of about ½ second and preferably less than 0.3 second, and down to less than 0.1 second. The delay time of the time delay stage 54 is preferably so selected that the pulse V generated by the M-FF 56, upon breathing at normal breathing rate, falls approximately within the first half of the inhaling phase of the breathing cycle.

Providing compressed air from the compressed air source 42 at a controlled rate permits operation of the aerosol fog generators or atomizers 32, 34 at an optimum operating range to generate fog droplets or atomized drops of such size that they can be optimally accepted by the patient.

Control of the transfer switch 58 is additionally supervised by the absolute flow rate; in some tests, it may be desirable to control the threshold stage 50, after suitable signal processing, directly from the pressure measuring element 24 which produces an output signal representing the rate of air flow in the tube 12. In this mode the switch 58 will be controlled by the magnitude of the flow signal. The pressure signal is directly representative of the flow because a flow through a resistance element such as element 16, generates a representative pressure.

The counter 60 can be integrated in the evaluation and output stage 28 if the stage 28 includes sufficient computation capacity to permit separate counter outputs. The transfer switch 58 can be constructed to have more than two switching positions, so that it has one OFF position corresponding to the full-line position shown in FIG. 3, and one connection to one fog generator, corresponding to the broken-line position; or to several fog generators, which can be controlled selectively, sequentially, or as desired, in accordance with switch programming, so that the switch can alternate between, for example, connection to a neutral aerosol (full-line position), and one of several selected irritating or testing aerosols.

The apparatus can operate with fixed dilution ratio of the irritant or testing substance of the aerosol, since adjustment of the quantity of the particular irritant or testing substance can be controlled by setting of the counter, that is, by controlling the ratio of breathing cycles in which aerosols with, and without, additive substances are introduced.

The dead space of the apparatus is small, so that practically only the portion of the breathing tube between the connection of the atomizers of aerosol fog generators and the mouthpiece is contacted with the aerosols, substantially facilitating cleaning. Change of substances to be applied to the test patient is simple and rapid, since the aerosol generators can be easily exchanged by rapid-connection couplers to the breathing tube 12. Additional aerosol generators—not shown—may be provided, one of which, for example, includes substances to counteract or to entrap aerosols which may provoke an asthmatic reaction.

The control of the apparatus, as aforesaid, and the system, has substantial advantages:

(1) The entire aerosol, which is generated only during the very short span of time $\Delta T_V$ is drawn along with the inhaling air and is entirely inhaled. This permits exact metering of the quantity being supplied, and thus the actual quantity inhaled by the patient is independent of the patient's breathing cycle;

(2) practically no aerosol will deposit within the breathing tube 12, since the aerosol is introduced only during a time that the patient is actually inhaling air, so that the aerosol is carried along with it. Consequently, contamination of the breathing tube and of the mouthpiece, as well as uncontrolled breathing-back of aerosols, is effectively and essentially avoided;

(3) practically no aerosol is breathed out or exhaled by the patient, since the entire aerosol will reach the alveoli. The oscillating air quantities within the lungs, the throat and the mouth will not have any aerosol contained therein since the actual injection of the aerosols into the air being inhaled occurred early in the breathing cycle. The air being exhaled, thus, hardly contains any unabsorbed aerosols.

Various changes and modifications may be made within the scope of the inventive concept.

I claim:

1. Diagnostic apparatus for testing the airways and pulmonary tract of a patient for sensitivity to specific substances administered in a first aerosol, said apparatus comprising
    a mouthpiece (14) adapted for breathing connection with the mouth of the patient;
    a single breathing tube duct means (12) having a first end coupled to said mouthpiece, and a second end communicating with a breathable gas;
    first atomizing means (34) for producing said first aerosol and having an operating energy inlet and a first aerosol outlet (34);
    second atomizing means (32) for producing a second aerosol differing from said first aerosol, and having an operating energy inlet and a second aerosol outlet (32);
    atomizing energy control means (38, 40, 42) coupled to both the atomizing means for selectively controlling application of atomizing energy from an energy input to said atomizing means;
    means for producing a signal corresponding to the gas flow in said breathing tube duct means and comprising airways resistance determination means including controllable flow resistance means (16, 18) in said duct means, and pressure sensor means (24) having an inlet (22) coupled to said duct means; and control means (30) coupled to the atomizing energy application control means and the airways resistance determination means;

wherein said breathing duct means has, in operation, continuously connected thereto in the order named from said first to said second ends:

(a) the first continuously open outlet (34a) from said first atomizing means, said first outlet being directly and continuously coupled to said duct means and being located directly adjacent the mouthpiece (14), (b) the second continuously open outlet (34a) from said second atomizing means, said second outlet being directly and continuously coupled to said duct means and being located directly adjacent the mouthpiece (14), (c) said pressure sensor inlet (22), and (d) the controllable flow resistance means (16, 18); said pressure sensor means (24) being coupled to said control means (30) for determination of airway resistance; and wherein said control means (30) is responsive to inhaling (IN) and exhaling (EX) breathing phases of the breathing cycle of the patient, and controls the supply of atomizing energy to the operating energy inlet of both said atomizing means to cause, selectively, introduction of the first aerosol into the breathing tube duct means during a portion only of the inhaling phase (IN) of at least one breathing cycle and selectively permit introduction of another aerosol during another breathing cycle while preventing contamination of the breathable gas by said first aerosol of the other aerosol, said atomizing energy causing atomization of the respective aerosol, and termination of supply of atomizing energy terminating vaporization of the selected aerosol.

2. Apparatus according to claim 1, wherein said control means (30) controls connection of said atomizing energy control means to both the atomizing means during the first two thirds of the inhaling phase of a breathing cycle.

3. Apparatus according to claim 1, wherein said control means (30) controls connection of said atomizing energy control means to at least one of the atomizing means during the first half of the inhaling phase of a breathing cycle.

4. Apparatus according to claim 1, including timing control means (56) connected to and controlling timing of the portion only during which the atomizing energy control means is connected to at least one of said atomizing means.

5. Apparatus according to claim 4, wherein the timing of said timing means controls application of said aerosol for a time period of about ½ second maximum.

6. Apparatus according to claim 4, wherein the timing of said timing means controls application of said aerosol for a time period of less than 0.3 second.

7. Apparatus according to claim 1,
including transfer switch means selectively enabling a selected one of the first or second atomizing means (32, 34) during said portions of the inhaling phase (IN).

8. Apparatus according to claim 7, including timing means connected to said transfer switch means to control the relative connection times of the respective atomizing means.

9. Apparatus according to claim 8, wherein the timing means comprises a counter (60) connected to the breathing tube duct means and counting the breathing cycles as the patient breathes through the mouthpiece, the counter means controlling the transfer switch means (58) to selectively connect one first or second one of the atomizing means in accordance with selected counts of the counter.

10. Apparatus according to claim 1, further including a timing circuit element (56) controlling the duration of the portion of the inhalation phase (IN), said timing circuit element being adjustable and providing for an adjustable period of time during which the atomizing energy control means provides atomizing energy to the respective atomizing means.

11. Apparatus according to claim 1, further comprising time delay means (54) responsive to the control means (30) and controlling the atomizing energy control means to supply atomizing energy to the atomizing means (32, 34) for injection of aerosols into the breathing tube adjacent the mouthpiece after a predetermined period of time ($\Delta t$) subsequent to commencement of the inhalation phase (IN) of the breathing cycle.

12. Apparatus according to claim 1 wherein the atomizing energy input comprises a compressed air source (42) and the atomizing energy control means comprises valve means (38, 40) connecting compressed air from the compressed air source to the respective atomizing means (32, 34).

13. Apparatus according to claim 1, wherein the atomizing means (32, 34) are coupled to the breathing tube duct means (12) by a quick coupling connection.

14. Apparatus according to claim 1, wherein the flow resistance measuring means includes a rapid operating valve (18) connected to the breathing tube duct means (12), and a pressure sensor (24) coupled to the breathing tube duct means to permit measurement of pulmonary tract air flow resistance.

15. Method of introducing two different additive aerosols into the airways and pulmonary tract of a patient (10) breathing a breathable gas through a breathing tube (12) having a mouthpiece, for testing sensitivity to specific substances administered in one of the aerosols comprising sensing initiation of the inhalation phase of a breathing cycle of the patient;

establishing a timing interval after initiation of the breathing phase;

introducing a first one of the aerosols into the inhaling gas immediately in advance of the mouthpiece after elapse of the timing interval and for a time duration which is less than the remaining time of a normal inhalation phase of the breathing cycle;

essentially continuously determining airways resistance;

introducing a second one of the aerosols into the inhaling air immediately in advance of the mouthpiece during a time when the first one of the aerosols is not being introduced, and wherein said aerosol introduction steps consist of vaporizing the selected one of the aerosols for the time duration that said aerosol is being introduced into the inhaling gas while maintaining continuous communication between the breathing tube and both aerosols.

16. Method according to claim 15,
and wherein said step of introducing one of the aerosols comprises introducing aerosols into the breathing tube during the first two thirds of the inhalation phase of a normal breathing cycle, preferably during the first half of said inhalation phase, and for a time duration of at the most ½ second.

17. Method according to claim 15, further including the step of counting the number of breathing cycles during testing of a patient;
and said step of introducing one of the aerosols comprises introducing said one of the aerosols only after a predetermined number of counts of breathing cycles.

18. Method according to claim 17, wherein said step of introducing the aerosols comprises introducing a controlled quantity of aerosols during said time duration.

19. Method according to claim 16, wherein said time duration is less than 0.3 seconds.

20. Apparatus for testing the airways and pulmonary tract of a patient (10) for sensitivity to different specific substances administered in respective ones of two aerosols comprising
a mouthpiece (14) adapted for breathing connection with the mouth of a patient;
a single breathing tube duct means (12) having a first end coupled to the mouthpiece; and a second end communicating with a breathing gas;
air flow analyzing and signal producing means (16, 18, 22, 24) for analyzing air flow through the breathing tube means to determine the beginning and end of inhalation (IN) and exhalation (EX) phases of the breathing cycles of the patient and for measuring the airways resistance of the pulmonary tract, coupled to the duct means, said analyzing means producing a signal corresponding to the gas flow in said duct means and including controllable flow resisting means (16, 18) in said duct means, and pressure sensor means (24) having an inlet (22) coupled to said duct means;
first atomizing means (34) including a first one of the aerosols, and having an outlet (34a) continuously open and coupled to the breathing tube duct means;
second atomizing means (32) including a second one of the aerosols, and having an outlet (32a) continuously open and coupled to the breathing duct means;
and control means (38, 40, 42) coupled and responsive to said flow analyzing means (16, 18, 22, 24) for selectively controlling application of atomizing energy to said first and second atomizing means as a function of inhaling (IN) and exhaling (EX) breathing phases of the breathing cycle of the patient,
said control means controlling said atomizing means (34) to selectively introduce aerosols into the breathing tube duct means only during selected portions of the inhaling phase (IN) of at least one breathing cycle;
time delay means (54) responsive to said control means and providing a predetermined period of time ($\Delta t$) subsequent to commencement of the inhalation phase (IN) of the breathing cycle of a patient as determined by said analyzing means, and controlling one (34) of the atomizing means to supply atomizing particles to the breathing tube upon expiration of said predetermined period of time;
and wherein the outlet (34a) from the first atomizing means is directly coupled to the mouthpiece (14) and located closely adjacent the mouthpiece;
the pressure sensor inlet (22) is coupled to the duct means between the outlet from the atomizing means (34) and the controllable flow resistance means (16, 18);
and the pressure sensor (24) is coupled to the control means for determination of airways resistance.

* * * * *

UNITED STATES PATENT AND TRADEMARK OFFICE
CERTIFICATE OF CORRECTION

PATENT NO.   :   4,558,710

DATED        :   Dec. 17, 1985

INVENTOR(S)  :   EICHLER

It is certified that error appears in the above-identified patent and that said Letters Patent is hereby corrected as shown below:

```
Claim 9, column 8, line 10, delete "one"
Claim 17, column 9, line 13, delete "and"
Description, Column 4, line 61, change "20" to -- 22 --
```

Signed and Sealed this

Sixteenth Day of September 1986

[SEAL]

Attest:

Attesting Officer

DONALD J. QUIGG

Commissioner of Patents and Trademarks